(12) United States Patent
Nakazumi

(10) Patent No.: US 10,321,947 B2
(45) Date of Patent: Jun. 18, 2019

(54) LIVING BODY HEATING INSTRUMENT AND CONTROL DEVICE

(71) Applicant: AD ME TECH CO., LTD., Matsuyama-shi, Ehime (JP)

(72) Inventor: Shinichi Nakazumi, Ehime (JP)

(73) Assignee: AD ME TECH CO., Ltd., Ehime (JP)

(*) Notice: Subject to any disclaimer, the term of this patent is extended or adjusted under 35 U.S.C. 154(b) by 0 days.

(21) Appl. No.: 14/778,710

(22) PCT Filed: Mar. 10, 2014

(86) PCT No.: PCT/JP2014/056129
§ 371 (c)(1),
(2) Date: Sep. 21, 2015

(87) PCT Pub. No.: WO2014/148289
PCT Pub. Date: Sep. 25, 2014

(65) Prior Publication Data
US 2016/0051312 A1    Feb. 25, 2016

(30) Foreign Application Priority Data

Mar. 22, 2013  (JP) .................................. 2013-059308

(51) Int. Cl.
*A61B 18/08*        (2006.01)
*A61B 18/00*        (2006.01)

(52) U.S. Cl.
CPC .... *A61B 18/082* (2013.01); *A61B 2018/0016* (2013.01); *A61B 2018/00482* (2013.01);
(Continued)

(58) Field of Classification Search
CPC ........... A61M 25/0067; A61B 17/3478; A61B 2018/143; A61B 18/1477; A61B 18/1425
See application file for complete search history.

(56) References Cited

U.S. PATENT DOCUMENTS

2002/0026127 A1* 2/2002 Balbierz ............ A61B 18/1206
600/567
2003/0073988 A1 4/2003 Berube et al.
(Continued)

FOREIGN PATENT DOCUMENTS

CN       201 719 369 U     1/2011
JP       S63-176426 U     11/1988
(Continued)

OTHER PUBLICATIONS

Apr. 1, 2014 Search Report issued in International Patent Application No. PCT/JP2014/056129.
(Continued)

*Primary Examiner* — Eun Hwa Kim
(74) *Attorney, Agent, or Firm* — Oliff PLC

(57) ABSTRACT

A living body heating instrument is pushed or inserted into an affected part to continuously perform cauterization and vaccinotherapy. A living body heating instrument that is pushed or inserted into an affected part of a living body to heat the affected part includes: an inner needle; and an outer needle having a hollow portion into which the inner needle is inserted through an opening at the needle base side toward the needle tip side. The inner needle has biocompatibility and thermal conductivity, and contains a heater. The affected part is cauterized by the heater with the inner needle inserted in the outer needle. Next, the inner needle is withdrawn, and a drug is injected through the outer needle, which remains inserted, to perform immunotherapy. A temperature detecting element may be provided in an inner part of the inner needle or on an outer surface of the outer needle.

9 Claims, 5 Drawing Sheets

(52) U.S. Cl.
CPC ............... *A61B 2018/00541* (2013.01); *A61B 2018/00595* (2013.01); *A61B 2018/00791* (2013.01)

(56) References Cited

U.S. PATENT DOCUMENTS

| | | | |
|---|---|---|---|
| 2003/0212394 A1* | 11/2003 | Pearson | A61B 18/1477 606/41 |
| 2005/0267465 A1* | 12/2005 | Hillier | A61B 18/1477 606/41 |
| 2007/0125662 A1* | 6/2007 | Dumont | A61B 18/1477 205/701 |
| 2009/0292259 A1* | 11/2009 | Delano | A61B 17/3401 604/263 |
| 2011/0054455 A1 | 3/2011 | Lee et al. | |

FOREIGN PATENT DOCUMENTS

| | | |
|---|---|---|
| JP | 2008-099923 A | 5/2008 |
| JP | 2010-205680 A | 9/2010 |
| JP | 5147004 B2 | 2/2013 |
| WO | 2011/037235 A1 | 3/2011 |

OTHER PUBLICATIONS

Nov. 11, 2016 Extended European Search Report issued in European Patent Application No. 14767430.3.

* cited by examiner

LIVING BODY HEATING INSTRUMENT AND CONTROL DEVICE

BACKGROUND OF THE INVENTION

Field of the Invention

The present invention relates to a living body heating instrument whose needle section is pushed or inserted into an affected part of a living body to heat the affected part and to a control device for controlling such a living body heating instrument. The present application claims priority based on Japanese Patent Application No. 2013-059308 filed in Japan on Mar. 22, 2013. The total contents of the Patent Application are to be incorporated by reference into the present application.

Description of Related Art

In the treatment of cancer or the like, cauterization may be performed as local treatment. As a method of such cauterization, the applicant of the present invention has proposed Patent document 1. In Patent document 1, a needle section containing a heater is pushed or inserted into an affected part, and the affected part is cauterized by being heated by the heater.

Incidentally, at stage III or IV of lung cancer, pancreatic cancer, or the like, it is often difficult to perform a surgical removal and it is common to perform anticancer drug treatment or radiation therapy. Further, especially at the terminal stages, minimally invasive treatment is desired for a reduction in burden on patients, if surgical treatment is performed at all.

PRIOR-ART DOCUMENTS

Patent Document

Patent document 1: International Publication No. 2011/037235

BRIEF SUMMARY OF THE INVENTION

Problems to be Solved by the Invention

It is an object of the present invention to provide a minimally invasive living body heating instrument that can be pushed or inserted into an affected part to surely heat the affected part.

Further, it is another object of the present invention to provide a control device for controlling such a living body heating instrument.

Means to Solve the Problem

In order to attain the foregoing objects, a living body heating instrument according to the present invention that is pushed or inserted into an affected part of a living body to heat the affected part includes: an inner needle; and an outer needle having a hollow portion into which the inner needle is inserted through an opening at a needle base side toward a needle tip side. Moreover, the inner needle has biocompatibility and thermal conductivity, and contains a heater. It should be noted the inner needle may further contain a temperature detecting element. Alternatively, a temperature detecting element may be provided on an outer surface of the outer needle to more accurately measure the temperature of the affected part that is heated.

The outer needle may be configured, for example, as follows: the hollow portion of the outer needle may be a through-hole having openings at the needle tip and needle base of the outer needle or a hole having an opening only at the needle base. Alternatively, a heat insulating layer may be provided in a region on the outer surface of the outer needle, except for a region for heating the affected part, so as not to heat a part other than the affected part.

A control device for controlling such a living body heating instrument includes: a transmitting and receiving section that performs transmission and reception with the living body heating instrument; and a controller that controls a temperature and/or a heating time of the heater of the living body heating instrument that performs transmission and reception with the transmitting and receiving section. The controller may independently control the heaters of a plurality of the living body heating instruments. Further, the controller may control the heater in accordance with temperature data from a temperature detecting element.

Effects of Invention

According to the present invention, the living body heating instrument is pushed or inserted into a living body until it reaches an affected part, with the inner needle, which contains the heater, combined with the outer needle, and the heater is heated to cauterize the affected part. After the affected part has been cauterized, the living body heating instrument may be withdrawn. Alternatively, with the living body heating instrument pushed or inserted even after the affected part has been cauterized, the inner needle may be withdrawn from the outer needle, and a drug may be injected through the outer needle directly into the affected part that has been cauterized. The present invention makes it only necessary to push or insert a needle into an affected part without performing a laparotomy or the like, thus making it possible to achieve minimal invasion. Further, when a temperature detecting element is provided in an inner part of the inner needle or on an outer surface of the outer needle, it is possible to more finely control the temperature of the heater by feeding back temperature data to the control device. Furthermore, according to the present invention, when a plurality of the living body heating instruments are used, the heater of each individual living body heating instrument is independently controlled. This makes it possible to finely regulate the temperature of the heater according to the state of the place into which the needle has been pushed or inserted.

DETAILED DESCRIPTION OF THE INVENTION

Figure 1:
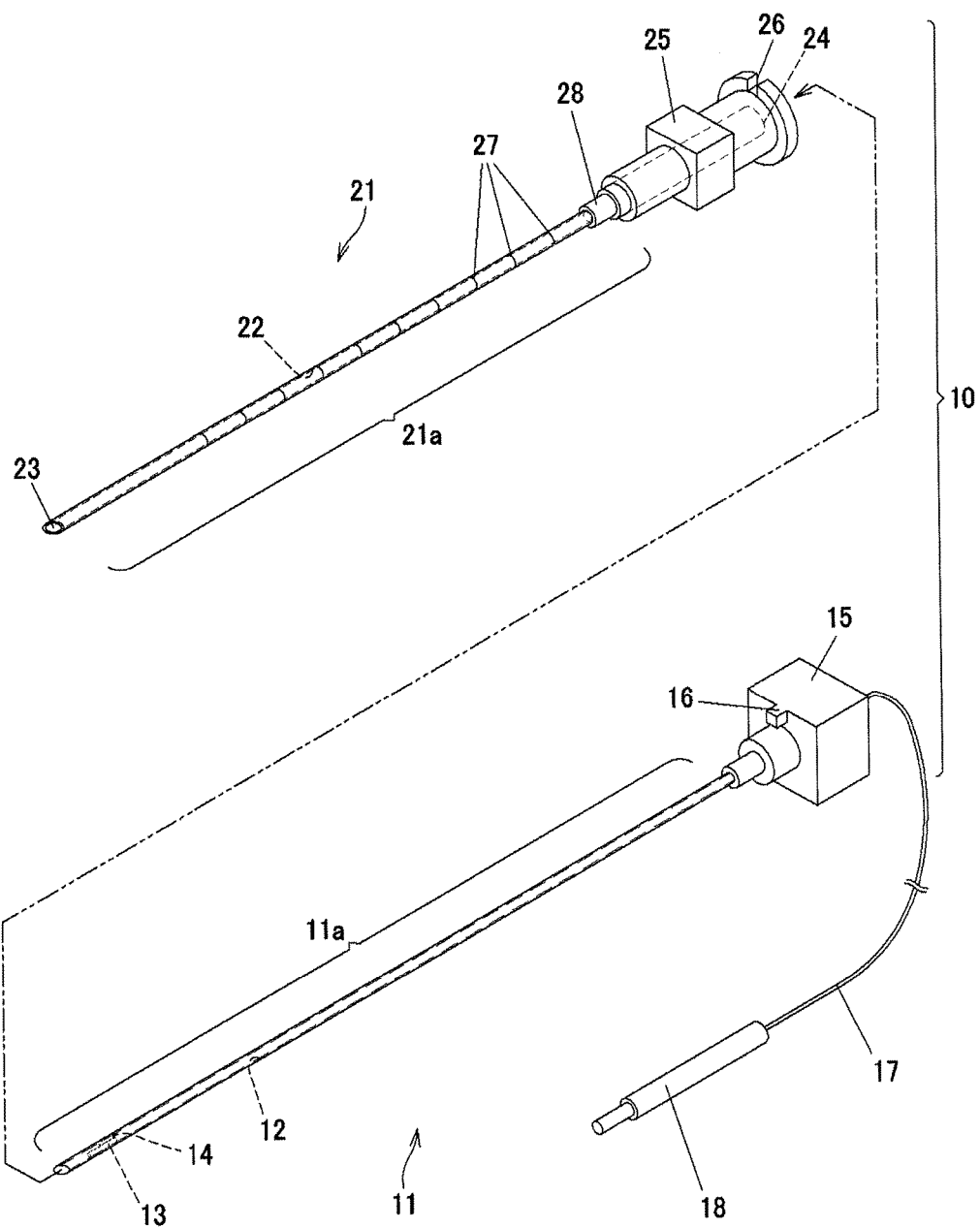
FIG. 1 is an exploded perspective view of a living body heating instrument to which the present invention is applied.
Figure 2:
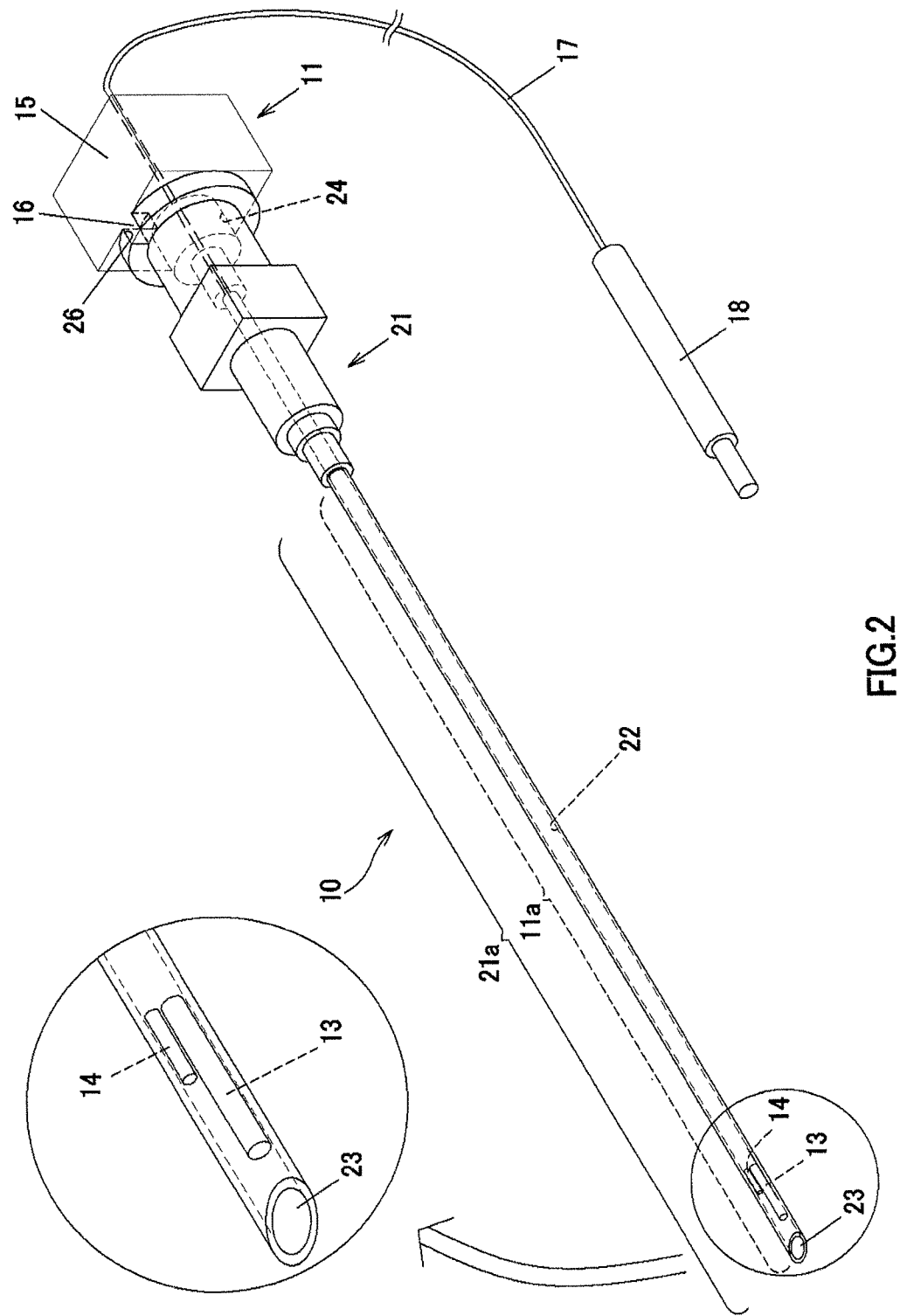
FIG. 2 is a perspective view of the living body heating instrument to which the present invention is applied.

A living body heating instrument to which the present invention is applied is described below with reference to the drawings. As shown in FIGS. 1 and 2, a living body heating instrument 10 includes an inner needle 11 and an outer needle 21 into which the inner needle 11 is inserted. With the inner needle 11 inserted in the outer needle 21, the living body heating instrument 10 is inserted into an affected part 1 of a living body in which lung cancer, pancreatic cancer, or the like has developed. The inner needle 11 and the outer needles 21 include needle sections 11a and 21a, respectively. These sections have biocompatibility, and are made of a metal material having excellent thermal conductivity. In this example, the metal material is stainless steel.

For example, the inner needle 11 has overall length of approximately 150 mm to 200 mm, and the needle section 11a has a diameter or thickness of approximately 0.3 mm to approximately 0.9 mm, preferably approximately 0.45 mm. The needle section 11a of the inner needle 11 includes a hollow portion 12 and a heater 13 installed in a part of the hollow portion 12 located at the needle tip side. The heater 13 takes the form of continuous filaments having a thickness of 0.5 mm or smaller, and has flexibility. The filamentous heater 13 is inserted into the hollow portion 12 of the needle section 11a through an opening located at the needle base side, and is installed at the needle tip side, where the affected part 1 is cauterized. It should be noted that in the hollow portion 12, a temperature detecting element 14 such as a thermocouple or a Peltier element, as well as the heater 13, may be installed to detect the temperature of the part of the needle section 11a located at the needle tip side, in order to enable a control device 30 to control the temperature of the needle section 11a. For example, in a case where the temperature detecting element 14 is a thermocouple, the temperature detecting element 14 is installed in the hollow portion 12 while being insulated from the heater 13 by an insulator such as a polyimide tube. For example, one or more of the heaters 13 may be provided in the hollow portion 12 of the needle section 11a. The heater 13 and the temperature detecting element 14 may be arranged in a longitudinal direction of the inner needle 11, or may be arranged in a radial direction of the inner needle 11. In a case where the heater 13 and the temperature detecting element 14 are arranged in the radial direction, the temperature detecting element 14 can detect temperature on the heater 13. By keeping the heater 13 and the temperature detecting element 14 apart from each other with a heat insulating material or the like, the temperature detecting element 14 can be protected from heat from the heater 13. Alternatively, for any treatment purpose, the heater 13 may be installed in any part of the inner needle 11 other than the distal end. At the edge of the inner needle 11, the hollow portion 12 is closed by biocompatible resin or the like.

The inner needle 11 includes a connection cord 17 connected to the heater 13 and the temperature detecting element 14 and derived from the needle base side. Provided at the end of the connection cord 17 is a plug 18 that is to be connected to the control device 30. The inner needle 11 includes a needle base section 15 made of a synthetic resin material such as polymethylpentene or polypropylene, which has electrical insulating properties and biocompatibility, or a metal material prepared by plating brass with nickel or the like. The needle base section 15 of the inner needle 11 is thicker than the needle section 11a. The needle base section 15 serves as an inner needle operating section that makes it easy to withdraw the inner needle 11 from the outer needle 21 with a medical instrument such as a probe or by hand. The needle base section 15 is also closed so that no moisture enters the hollow portion 12. Further, the inner needle 11 has its edge cut so that the inner needle 11 has an inclined edge surface, and the edge is sharply pointed. Of course, the edge surface is not limited to such a shape.

The outer needle 21, into which the inner needle 11 is inserted, has substantially the same length as the inner needle 11, i.e. an overall length of approximately 150 mm to 200 mm, so as to have its edge aligned with the edge of the inner needle 11 when the inner needle 11 has been inserted into the outer needle 21. Further, the outer needle 21 includes a needle section 21a formed in the shape of a cylinder to have a thickness, for example, of approximately 18 G (outer diameter 1.2 mm/inner diameter 0.94 mm) to 23 G (outer diameter 0.65 mm/inner diameter 0.4 mm). The needle section 21a of the outer needle 21 includes a hollow portion 22 at the end of which an edge opening 23 is formed and at the needle base of which a needle base opening 24 is formed to serve as a through hole. The outer needle 21 includes a needle base section 25 made of a synthetic resin material such as polymethylpentene or polypropylene, which has electrical insulating properties and biocompatibility, or a metal material prepared by plating brass with nickel or the like. The needle base section 25 of the outer needle 21 is thicker than the needle section 21a. The needle base section 25 serves as an outer needle 21 operating section that makes it easy to push or insert the living body heating instrument 10 into the affected part 1 and withdraw the living body heating instrument 10 from the affected part 1 with a medical instrument such as a probe or by hand. Further, the outer needle 21 has its edge cut so that the outer needle 21 has an inclined edge surface, and the edge is sharply pointed. Of course, the edge surface is not limited to such a shape.

The needle base section 15 of the inner needle 11 is fitted in the needle base section 25 of the outer needle 21. The needle base section 15 of the inner needle 11 includes a positioning protrusion 16, and the needle base section 25 of the outer needle 21 includes a positioning depression 26. When the needle base section 15 of the inner needle 11 is fitted in the needle base section 25 of the outer needle 21, the positioning protrusion 16 of the needle base section 15 of the inner needle 11 engages with the positioning depression 26 of the needle base section 25 of the outer needle 21, whereby rotation is arrested and circumferential positioning effected. Once positioning is effected, the inclined edge surface at the edge of the inner needle 11 and the inclined edge surface at the edge of the outer needle 21 become flush with each other. Alternatively, the needle base section 25 of the outer needle 21 may include a positioning protrusion 16, and the needle base section 15 of the inner needle 11 may include a positioning depression 26.

The needle section 21a of the outer needle 21 has graduations 27 formed at predetermined intervals on a surface of the needle section 21a to serve as a yardstick against which to push or insert the living body heating instrument 10 into the affected part 1, and also has an index member 28 slidably fitted on the needle section 21a. By moving the index member 28 along the needle section 21a of the outer needle 21, a user can use the index member 28, in relation with the graduations 27, as a yardstick for recognizing how deeply the user pushes or inserts the living body heating instrument 10 into the affected part 1.

Figure 3:
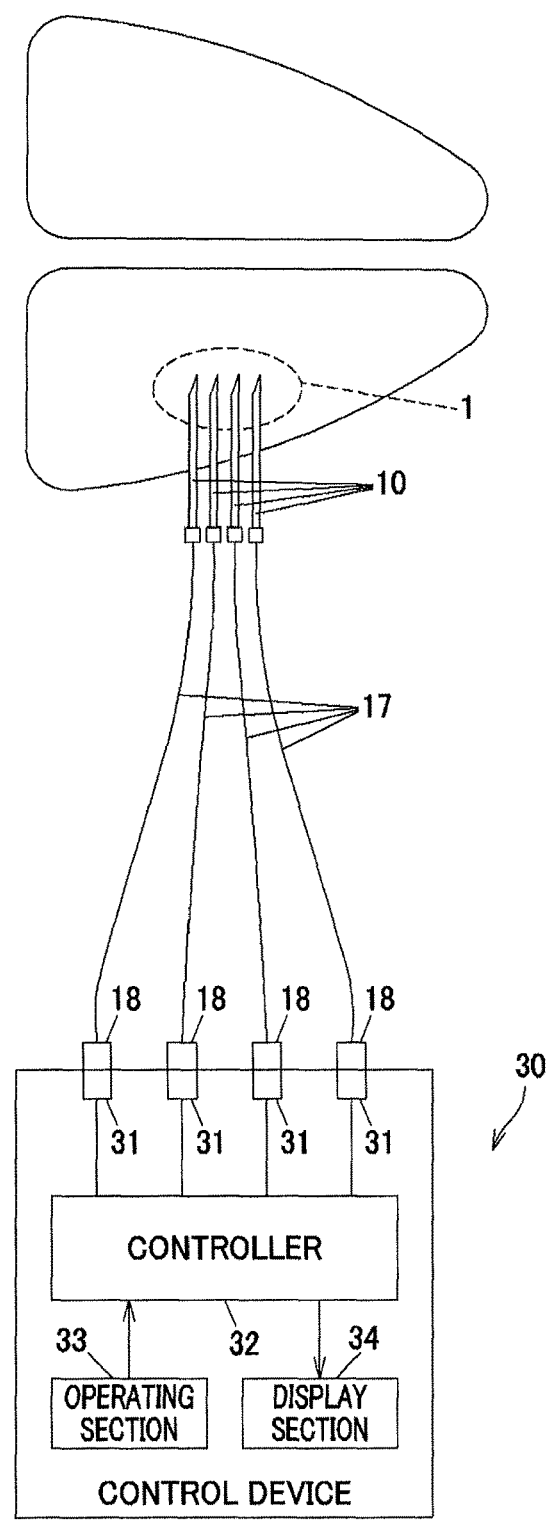
FIG. 3 shows the living body heating instrument and a control device to which the present invention is applied, and conceptually shows cauterization.

As shown in FIGS. 1 to 3, the living body heating instrument 10 is configured such that the inner needle 11 is inserted in the hollow portion 22 of the outer needle 21, that the needle base section 15 of the inner needle 11 is fitted in the needle base section 25 of the outer needle 21, that the positioning protrusion 16 engages with the positioning depression 26, whereby circumferential positioning is effected, and, furthermore, that the inclined edge surface at the inner edge and the inclined edge surface of the outer needle 21 are flush with each other. At the time of treatment, the plug 18 of the connection cord 17 derived from the needle base section 15 of the inner needle 11 is connected to the control device 30, with the inner needle 11 combined with the outer needle 21.

The control device 30 includes: terminal sections 31 which serve as transmitting and receiving sections and to which the plugs 18 of a plurality of living body heating instruments 10 are connected; a controller 32 that controls the plurality of living body heating instruments 10; an operating section 33 via which operation signals to operate the living body heating instruments 10 are inputted to the controller 32; and a display section 34 that displays a status of operation. The operating section 33 is provided with switches whose number is the same as the number of terminal sections 31. Each of the switches is constituted by a dial switch, a slide switch, or the like. The switches are used to independently control the temperature of the heater 13 of each living body heating instrument 10. This allows the user, for example, to regulate the temperature of the heat 13 of each living body heating instrument 10 by operating the operation section 33 while looking at the temperature of the heat 13 of each living body heating instrument 10 as displayed by the display section 34.

For example, since cancer cells are weaker against heat than healthy cells, very high-temperature heating is not required. By controlling the living body heating instruments 10 so that the heaters 13 is for example at approximately 60° C. to apply such an amount of heat to the cancer cells that proteins are irreversibly thermally denatured, the cancer cells can be cauterized with minimum damage to the healthy cells. Further, when a temperature detecting element 14 is provided in each needle section 11a, temperature data is supplied from the temperature detecting elements 14 to the controller 32, and the controller 32 controls the heaters 13 so that the heating temperature is kept constant. For example, even in the presence of a partial temperature loss due to blood flowing in the place into which the living body heating instruments 10 have been pushed or inserted, the affected part 1 can be entirely heated to the desired temperature, as the temperature of the heater 13 of each individual living body heating instrument 10 can be regulated. It should be noted, furthermore, that the controller 32 may contain a timer to turn off the heaters 13 when a period of time of cauterization set by the operating section 33 has elapsed.

Exchange of heater 13 control data and heater 13 temperature data between the living body heating instruments 10 and the control device 30 may be done by cable, or may alternatively be done by wireless. Further, the supply of electric power to the heaters 13 may be done by supplying electric power to the heaters 13 by cable from the control device 30 or from a primary or secondary battery provided in each living body heating instrument 10.

Figure 4:
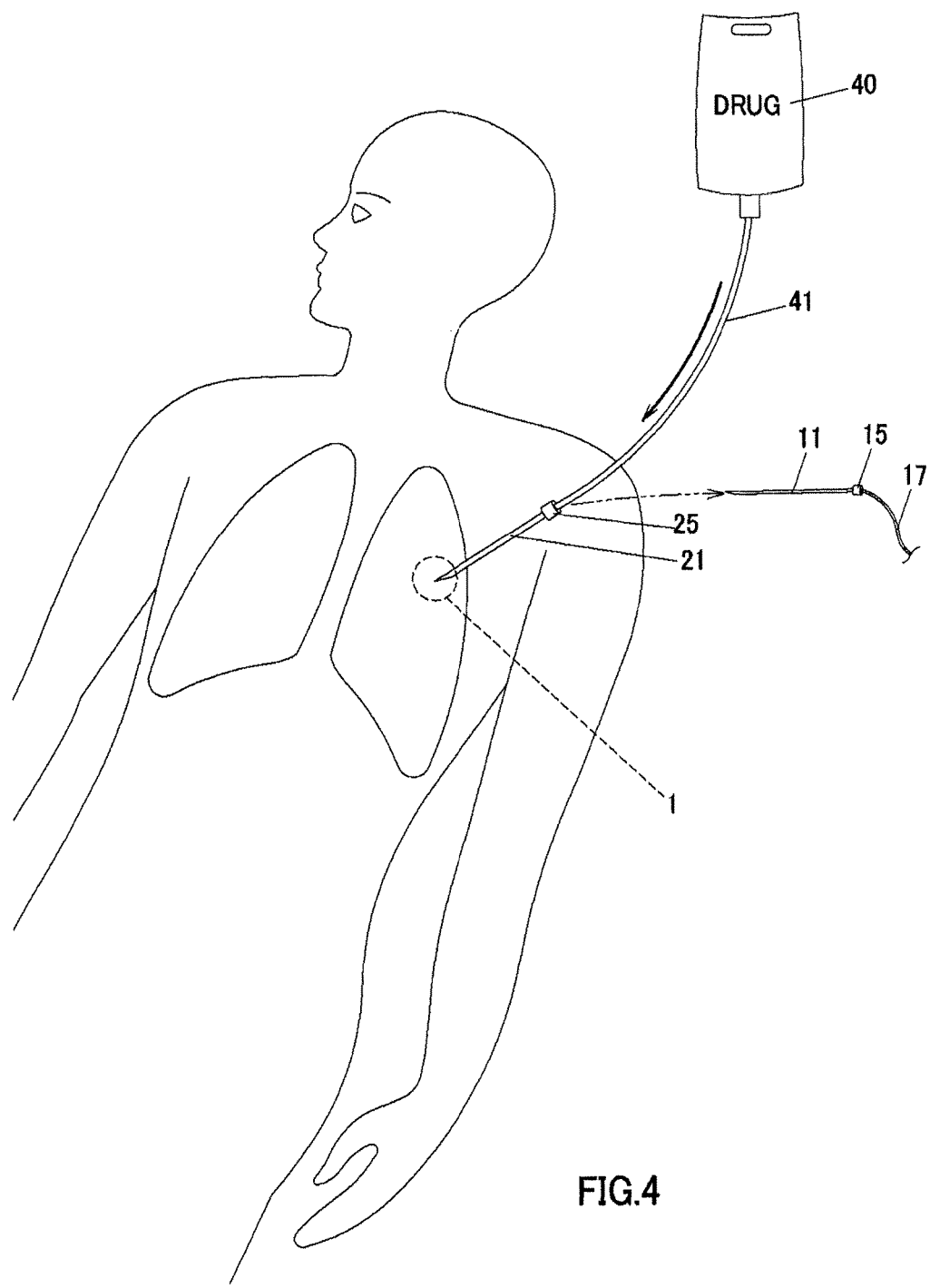
FIG. 4 conceptually shows a therapy in which a drug is injected directly into an affected part that has been cauterized.

As shown in FIG. 4, in performing cauterization, an affected part 1 of a living body in which lung cancer, pancreatic cancer, or the like has developed, i.e. a target into which a living body heating instrument 10 is to be pushed, is first identified and observed, and the route through which the living body heating instrument 10 is pushed, the temperature at which the affected part 1 is cauterized, the period of time of cauterization, and the like are then determined. Next, the living body heating instrument 10 is taken out of a container. The needle base section 25 of the outer needle 21 is fixed to a medical instrument such as a probe, and the plug 18 of the connection cord 17 derived from the needle base section 15 of the inner needle 11 is connected to a terminal section 31 of a control device 30. Before the living body heating instrument 10 is pushed or inserted into the affected part 1, the index member 28 and the graduations 27 of the outer needle 21 are used to set a yardstick of how deeply the living body heating instrument 10 is pushed or inserted. Next, while the direction and depth of needle insertion are confirmed with an echo on an ultrasound image of the living body heating instrument 10, under X-ray fluoroscopy, or under CT guidance, the needle tip is pushed or inserted into the affected part 1 thus identified. The living body heating instrument 10 is pushed or inserted into the affected part 1 with the inner needle 11 inserted in the outer needle 21. With the outer needle 21 alone, the outer needle 21 may bend when pushed or inserted and thus have difficulty in being pushed or inserted into the target position. Insertion of the inner needle 11 into the outer needle 21 makes it hard for the outer needle 21 to bend. This allows the needle tip of the living body heating instrument 10 to accurately reach the affected part 1.

Alternatively, in performing cauterization, the outer needle 21 alone may first be pushed or inserted into the affected part 1, and the inner needle 11 may then be inserted into the outer needle 21, if the outer needle 21 has a sufficient physical strength to be pushed or inserted into the affected part 1.

Next, the affected part 1 is cauterized for the predetermined period of time by operating the operating section 33 of the control device 30 to cause the heater 13 to generate heat to heat the needle tip portion of the outer needle 21 to the predetermined cauterization temperature. In so doing, the controller 32 can independently control the heater 13 of each living body heating instrument 10 in accordance with temperature data fed back from the temperature detecting element 14. Therefore, for example, even in the presence of a partial temperature loss due to blood flowing in the place into which the living body heating instrument 10 has been pushed or inserted, the affected part 1 can be entirely heated to the desired temperature. In this way, simply by being pushed or inserted into an affected part 1 located in a deep portion of a living body, the living body heating instrument 10 can cauterize the affected part 1. This makes it possible to perform minimally invasive cauterization on a patient.

Upon completion of cauterization of the affected part 1, the living body heating instrument 10 may be simply withdrawn from the affected part 1. In this example, however, after cauterization, the inner needle 11 is withdrawn from the living body heating instrument 10 pushed into the affected part 1. Then, in order to supply a drug 40 that is used in immunotherapy, a tube 41 of an intravenous drip or the like is connected to the needle base opening 24 of the outer needle 21, and the drug 40 is passed through the hollow portion 22 of the outer needle 21 and injected through the edge opening 23 into the affected part 1. An example of the immunotherapy is dendritic cell vaccinotherapy. This therapy makes it possible to perform immunotherapy by injecting the drug 40, such as a vaccine containing dendritic cells, into the affected part 1 that has been cauterized. Such direct injection of a drug 40 into an affected part 1 that has been cauterized can lead to effective treatment. Such treatment is effective especially against recurrent advanced cancer and the like.

It should be noted that usable examples of drugs 40 that are injected through the needle base section 25 of the outer needle 21 are not limited to those named above, but may include various types of drug 40, such as anticancer drugs 40, depending on the courses of treatment of patients. The living body heating instrument 10 makes it possible to continuously perform a therapy in which an affected part 1 is cauterized and a therapy in which a drug 40 is injected directly into the affected part 1 that has been cauterized. This makes it possible to perform minimally invasive treatment on a patient. Further, in a case where the living body heating instrument 10 is used exclusively for cauterizing an affected part 1, it is not necessary to inject a drug 40 into the affected part 1 that has been cauterized. In this case, the edge opening 23 of the outer needle 21 may be closed, and the hollow portion 22 of the outer needle 21 may be a hole opening only at the needle base opening 24.

As described above, the living body heating instrument 10 is pushed or inserted into a living body until it reaches an affected part 1, with the inner needle 11, which contains the heater 13, combined with the outer needle 21, and the heater 13 is heated to cauterize the affected part 1. At this point, the living body heating instrument 10 may be withdrawn. Alternatively, with the living body heating instrument 10 pushed or inserted, the inner needle 11 may be withdrawn from the outer needle 21, and a drug 40 may be injected through the outer needle 21 directly into the affected part 1 that has been cauterized. This makes it only necessary to push or insert the living body heating instrument 10 into the affected part 1 without performing a laparotomy or the like, thus making it possible to achieve minimal invasion. Further, there is no risk of exposure unlike in the case of radiation therapy, nor does a patient feel pain or have numbness unlike in the case of radiofrequency treatment.

Furthermore, when the inner needle 11 contains a temperature detecting element 14, it is possible to more finely control the temperature of the heater 13 by feeding back temperature data to the control device 30. Furthermore, when a plurality of the living body heating instruments 10 are used, the heater 13 of each individual living body heating instrument 10 is independently controlled. This makes it possible to finely regulate the temperature of the heater 13 according to the state of the place into which the living body heating instrument 10 has been pushed or inserted.

Figure 5:
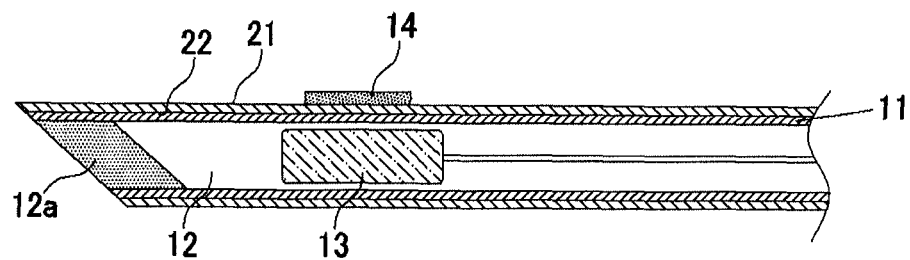
FIG. 5 is a cross-sectional view of main components of a modification of a living body heating instrument to which the present invention is applied, with a temperature detecting element provided on an outer surface of an outer needle.

The foregoing description has been given by taking, as an example, a case where the inner needle 11 contains a temperature detecting element 14. Alternatively, a temperature detecting element 14 may be provided on an outer surface of the outer needle 21. For example, as shown in FIG. 5, a temperature detecting element 14 is provided on the outer surface of the outer needle 21 so as to be located near the heater 13 when the inner needle 11 has been inserted. The temperature detecting element 14 is fixed on the outer surface of the outer needle 21 by a biocompatible adhesive or resin. In a case where the inner needle 11 contains a temperature detection element 14, the interposition of the outer needle 21, a minute gap between the outer needle 21 and the inner needle 11, and the inner needle 11 causes a temperature difference between the temperature measured in the inner needle 11 and the actual heating temperature of the affected part 1. On the other hand, in a case where a temperature detecting element 14 is provided on the outer surface of the outer needle 21 so as to be located near the heater 13, the temperature detecting element 14 makes contact with the affected part 1 being heated and can therefore more accurately measure the heating temperature of the affected part 1. Further, in the example shown in FIG. 5, where the inner needle 11 is provided with a heater 13 but not with a temperature detecting element 14, the needle base section 15 can be reduced in size to improve the operability of the inner needle 11. In this case, a connection cord 17 connecting the temperature detecting element 14 with the control device 30 and extending from the temperature detecting element 14 is derived from the needle base section 25 of the outer needle 21. The temperature detecting element 14 and the connection cord 17 are covered with a biocompatible material. It should be noted that the inner needle 11 has its distal end closed by a closing member 12a made of a biocompatible resin or the like.

Figure 6:
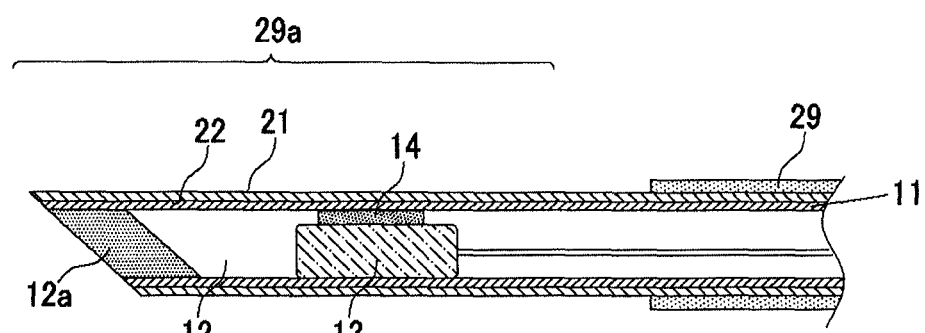
FIG. 6 is a cross-sectional view of main components of a modification of a living body heating instrument to which the present invention is applied, with a heat insulating layer provided on an outer surface of an outer needle.

Further, as mentioned above, the inner needle 11 and the outer needle 21 are often made of a biocompatible metal material such as stainless steel and therefore have excellent thermal conductivity. Therefore, for example, even in a case where the inner needle 11 contains a heater 13 at its distal end, thermal conductivity enables a rise in temperature even in a region of the outer needle 21 other than the distal end and at the midpoint of the outer needle 21. In this case, there is a risk of excessively heating a region other than the affected part 1. In general, a heating region of the living body heating instrument 10 that is pushed or inserted into the affected part 1 to cauterize the affected part 1 is often provided only at the distal end or provided to extend several millimeters from the tip. Accordingly, as shown in FIG. 6, a heat insulating layer 29 may be provided in a region on the outer surface of the outer needle 21, except for a heating region 29a for heating the affected part 1. For example, the heat insulating layer 29 may be made of biocompatible carbon fiber, ceramic, resin, or the like. In the example shown in FIG. 6, the distal end of the outer needle 21 serves as the heating region 29a, the heat insulating layer 29 is provided closer to the needle base side than the distal end, and the outer surface of the outer needle 21 is exposed in the heating region 29a. This allows only the heating region 29a to be heated to the heating temperature at which the affected part 1 is cauterized and makes it possible to suppress a rise in temperature in the other regions and thus prevent a region other than the affected part 1 from being excessively heated. It should be noted that the range of the heating region 29a is determined depending on the intended use. For example, the heating region 29a may be provided not at the distal end but at the midpoint of the needle, or may be a region extending from the distal end to the midpoint.

Figure 7:
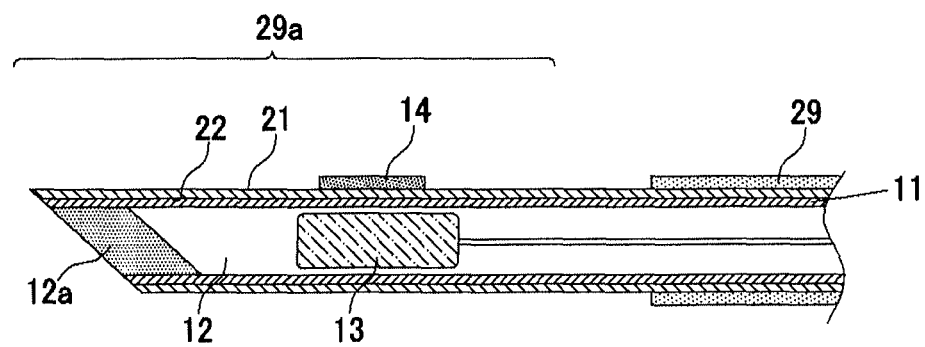
FIG. 7 is a cross-sectional view of main components of a modification of a living body heating instrument to which the present invention is applied, with a temperature detecting element and a heat insulating layer provided on an outer surface of an outer needle.

In the example shown in FIG. 7, a temperature detecting element 14 is provided on an outer surface of the outer needle 21, and a heat insulating layer 29 is provided on the outer surface of the outer needle 21. With this, as shown in FIG. 7, the temperature of an affected part 1 that is cauterized can be accurately measured by the temperature detecting element 14, and a part other than the affected part 1 can be prevented from being heated by a region other than the heating region 29a.

The living body heating instrument 10 can be used in the treatment of various types of cancer such as uterus cancer and cervical cancer as well as the aforementioned lung cancer and pancreatic cancer. Further, the living body heating instrument 10 can also be used for heating an affected part of a non-human animal.

REFERENCE SYMBOLS 1 affected part, 10 living body heating instrument, 11 inner needle, 11a needle section, 12 hollow portion, 12a closing member, 13 heater, 14 temperature detecting element, 15 needle base section, 16 positioning protrusion, 17 connection cord, 18 plug, 21 outer needle, 21a needle section, 22 hollow portion, 23 edge opening, 24 needle base opening, 25 needle base section, 26 positioning depression, 27 graduations, 28 index member, 29 heat insulating layer, 29a heating region, 30 control device, 31 terminal section, 32 controller, 33 operating section, 34 display section, 40 drug, 41 tube

The invention claimed is:

1. A living body heating instrument configured to be pushed or inserted into an affected part of a living body to heat the affected part, comprising:
    an inner needle having biocompatibility and thermal conductivity, wherein the inner needle comprises:
        a hollow portion;
        an inner needle base section including a positioning protrusion;
        a heater disposed within the hollow portion, wherein the heater is formed of filaments and having flexibility; and
        a temperature detecting element arranged directly adjacent to the heater and disposed within the hollow portion, wherein the temperature detecting element and the heater are arranged in parallel in a longitudinal direction of the inner needle; and
    an outer needle having a hollow portion into which the inner needle is inserted through an opening at a needle base side toward a needle tip side; and an outer needle base section including a positioning depression;
    wherein the outer needle is injectable with a drug and an overall length of the outer needle is 150 mm to 200 mm and a thickness of the outer needle is 18G to 23G; and
    wherein a tip of the inner needle does not protrude from a tip of the outer needle by configuring a cutting edge of the outer needle to be aligned with a cutting edge of the inner needle such that an inclined edge surface of the inner needle and an inclined edge surface of positioning depression.

2. The living body heating instrument according to claim 1, further comprising a heat insulating layer provided in a region on the outer surface of the outer needle, except for a heating region for heating the affected part of the living body.

3. The living body heating instrument according to claim 1, wherein the hollow portion is a through-hole penetrating from the opening of the needle tip to the opening of the needle base of the outer needle.

4. The living body heating instrument according to claim 1, wherein the temperature detecting element is a thermocouple or a Peltier element.

5. A control system comprising: (1) a control device for controlling a living body heating instrument, and (2) the living body heating instrument connected thereto, the living body heating instrument configured to be pushed or inserted into an affected part of a living body to heat the affected part,
    the living body heating instrument including:
        an inner needle having biocompatibility and thermal conductivity, wherein the inner needle comprises:
            a hollow portion;
            an inner needle base section including a positioning protrusion;
            a heater disposed within the hollow portion, wherein the heater is formed of filaments and having flexibility; and
            a temperature detecting element arranged directly adjacent to the heater and disposed within the hollow portion, wherein the temperature detecting element and the heater are arranged in parallel in a longitudinal direction of the inner needle; and
        an outer needle having a hollow portion into which the inner needle is inserted through an opening at a needle base side toward a needle tip side; and an outer needle base section including a positioning depression;
    wherein the outer needle is injectable with a drug and an overall length of the outer needle is 150 mm to 200 mm and a thickness of the outer needle is 18G to 23G; and
    wherein a tip of the inner needle does not protrude from a tip of the outer needle by configuring a cutting edge of the outer needle to be aligned with a cutting edge of the inner needle such that an inclined edge surface of the inner needle and an inclined edge surface of positioning depression;
    wherein the control device comprises:
    a transmitting and receiving section that performs transmission and reception with the living body heating instrument; and
    a controller that controls a temperature and/or a heating time of the heater of the living body heating instrument that performs transmission and reception with the transmitting and receiving section.

6. The control system according to claim 5, wherein:
    the controller controls the heater in accordance with temperature data from the temperature detecting element.

7. The control system according to claim 6, wherein the controller independently controls each heater of a plurality of the living body heating instruments.

8. The control system according to claim 5, wherein the controller independently controls each heater of a plurality of the living body heating instruments.

9. The control system according to claim 5, wherein the temperature detecting element is a thermocouple or a Peltier element.

* * * * *